(12) United States Patent
Wiemker et al.

(10) Patent No.: US 11,657,500 B2
(45) Date of Patent: May 23, 2023

(54) SYSTEM AND METHOD FOR ASSESSING A PULMONARY IMAGE

(71) Applicant: KONINKLIJKE PHILIPS N.V., Eindhoven (NL)

(72) Inventors: Rafael Wiemker, Kisdorf (DE); Tanja Nordhoff, Hamburg (DE); Thomas Buelow, Grosshansdorf (DE); Axel Saalbach, Hamburg (DE); Tobias Klinder, Uelzen (DE); Tom Brosch, Hamburg (DE); Tim Philipp Harder, Ahrensburg (DE); Karsten Sommer, Hamburg (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 16/955,959

(22) PCT Filed: Dec. 14, 2018

(86) PCT No.: PCT/EP2018/084890
§ 371 (c)(1),
(2) Date: Jun. 19, 2020

(87) PCT Pub. No.: WO2019/121369
PCT Pub. Date: Jun. 27, 2019

(65) Prior Publication Data
US 2020/0320705 A1    Oct. 8, 2020

(30) Foreign Application Priority Data
Dec. 20, 2017   (EP) ..................................... 17208950

(51) Int. Cl.
*G06T 7/00*    (2017.01)
*G06T 7/11*    (2017.01)
(Continued)

(52) U.S. Cl.
CPC .......... *G06T 7/0012* (2013.01); *A61N 5/1031* (2013.01); *G06T 5/002* (2013.01);
(Continued)

(58) Field of Classification Search
CPC ....... A61N 5/1031; G06T 7/0012; G06T 7/11; G06T 5/002; G06T 2207/10081;
(Continued)

(56) References Cited

U.S. PATENT DOCUMENTS 6,760,468 B1 *  7/2004  Yeh ........................ G16H 50/20
                                                                382/173
7,949,169 B2    5/2011  Bae
(Continued)

FOREIGN PATENT DOCUMENTS

JP    2003070778 A    3/2003
JP    2005198798 A    7/2005
(Continued)

OTHER PUBLICATIONS

PCT International Search Report, International Application No. PCT/EP2018/084890, dated Mar. 25, 2019.
(Continued)

*Primary Examiner* — Bobbak Safaipour
*Assistant Examiner* — Duy Tran
(74) *Attorney, Agent, or Firm* — Larry Liberchuk

(57) ABSTRACT

The invention relates to a system for assessing a pulmonary image which allows for an improved assessment with respect to lung nodules detectability. The pulmonary image is smoothed for providing different pulmonary images (20, 21, 22) with different degrees of smoothing, wherein signal values and noise values, which are indicative of the lung vessel detectability and the noise in these images, are determined and used for determining an image quality being indicative of the usability of the pulmonary image to be
(Continued)

assessed for detecting lung nodules. Since a pulmonary image shows lung vessels with many different vessel sizes and with many different image values, which cover the respective ranges of potential lung nodules generally very well, the image quality determination based on the different pulmonary images with different degrees of smoothing allows for a reliable assessment of the pulmonary image's usability for detecting lung nodules. The image quality is used to determine a radiation dose level to be applied for generating a next pulmonary image.

14 Claims, 7 Drawing Sheets

(51) Int. Cl.
*G06T 5/00* (2006.01)
*A61N 5/10* (2006.01)

(52) U.S. Cl.
CPC ...... *G06T 7/11* (2017.01); *G06T 2207/10081* (2013.01); *G06T 2207/20021* (2013.01); *G06T 2207/20182* (2013.01); *G06T 2207/30064* (2013.01); *G06T 2207/30168* (2013.01)

(58) Field of Classification Search
CPC . G06T 2207/20182; G06T 2207/30064; G06T 2207/30168
See application file for complete search history.

(56) References Cited

U.S. PATENT DOCUMENTS

| | | |
|---|---|---|
| 8,465,437 B2 | 6/2013 | Avila |
| 8,824,752 B1 | 9/2014 | Fonte |
| 2004/0151356 A1* | 8/2004 | Li ............................. G06T 7/11 382/131 |
| 2004/0184647 A1* | 9/2004 | Reeves ................. G06T 3/0075 382/131 |
| 2005/0171409 A1* | 8/2005 | Arimura ............... G06T 7/0012 378/10 |
| 2008/0002870 A1* | 1/2008 | Farag .................... G06K 9/6215 382/209 |
| 2016/0110584 A1* | 4/2016 | Remiszewski ......... G06V 20/69 382/133 |

FOREIGN PATENT DOCUMENTS

| | | |
|---|---|---|
| JP | 2013153824 A | 8/2013 |
| WO | 2015131962 A1 | 9/2015 |

OTHER PUBLICATIONS

Samei E. et al., "Size-Based Quality-Informed Framework for Quantitative Optimization of Pediatric CT", Journal of Medical Imaging, 4(3), 031209, Jul.-Sep. 2017.

Li X. et al., "Lung Nodule Detection in Pediatric Chest CT: Quantitative Relationship Between Image Quality and Radiologist Performance", Med. Phys., 38(5), May 5, 2011, pp. 2609-2618.

* cited by examiner

SYSTEM AND METHOD FOR ASSESSING A PULMONARY IMAGE

FIELD OF THE INVENTION

The invention relates to a system, method and computer program for assessing a pulmonary image.

BACKGROUND OF THE INVENTION

For the detection of lung nodules pulmonary images like computed tomography images of the lung are often used, wherein for assessing the image quality of a pulmonary image with respect to its usability for reliably detecting a lung nodule its noise might be determined. However, determining the image quality just based on the noise is often not good enough, because the detectability of lung nodules in a pulmonary image might also depend on other factors.

SUMMARY OF THE INVENTION

It is an object of the present invention to provide a system, method and computer program for assessing a pulmonary image, which allows for an improved assessment with respect to the detectability of a lung nodule in the pulmonary image.

In a first aspect of the present invention a system for assessing a pulmonary image is presented, wherein the system comprises:

a pulmonary image providing unit configured to provide a pulmonary image which comprises image elements to which image values are assigned and which shows lung vessels, a smoothing unit configured to smooth the provided pulmonary image for providing different pulmonary images with different degrees of smoothing, a signal value determination unit configured to determine signal values for the different pulmonary images, wherein for a respective pulmonary image one or more signal values, which are indicative of the detectability of the lung vessels in the respective pulmonary image, are determined based on the image values of the respective pulmonary image, a noise value determination unit configured to determine noise values for the different pulmonary images, wherein for a respective pulmonary image one or more noise values, which are indicative of the noise in the respective pulmonary image, are determined based on the image values of the respective pulmonary image, an image quality determination unit configured to determine an image quality for the provided unsmoothed image based on the signal values and noise values determined for the different pulmonary images.

In a pulmonary image lung vessels with many different vessel sizes and with many different image values like Hounsfield densities are present, which cover the respective ranges of potential lung nodules generally very well. Since the different pulmonary images correspond to different degrees of smoothing, which include, for instance, no smoothing and one or more different degrees of smoothing, in the different pulmonary images the distribution of sizes of the lung vessels is different, i.e., for instance, the "center of mass" of this distribution is shifted to larger sizes with increasing degree of smoothing. Thus, the signal values and noise values are determined for different distributions of sizes of the lung vessels in the different pulmonary images, wherein it has been found that by using these signal values and noise values for determining the image quality of the provided, unsmoothed pulmonary image, it can be very accurately determined whether the pulmonary image is suitable for detecting a lung nodule.

The pulmonary image providing unit can be a storing unit in which the pulmonary image is stored already and from which the pulmonary image can be retrieved. The pulmonary image providing unit can also be a receiving unit for receiving the pulmonary image from a pulmonary image generating system like a computed tomography system, wherein the pulmonary image providing unit can be adapted to provide the received pulmonary image. The pulmonary image providing unit can also be the pulmonary image generating system which generates the pulmonary image and which provides the generated pulmonary image. The provided pulmonary image is preferentially a computed tomography image which has been generated by applying a radiation dose to a patient. However, the pulmonary image can also be an image generated by another imaging modality, which also shows the lung vessels.

The smoothing unit is configured to perform a spatial smoothing of the image values assigned to the image elements. This smoothing can be a Gaussian smoothing or another kind of smoothing. The smoothing unit can be adapted to generate one smoothed pulmonary image or several smoothed pulmonary images, wherein the several smoothed pulmonary images are smoothed to different degrees of smoothing. For determining the image quality the image quality determination unit preferentially uses the one or more differently smoothed pulmonary images and preferentially also the provided, unsmoothed pulmonary image.

In an embodiment the signal value determination unit is configured to segment the lung vessels in a respective pulmonary image based on the image values of the respective pulmonary image, to determine one or several lung vessel values being indicative of the amount of lung vessels in the respective pulmonary image based on the segmented lung vessels and to determine the one or several signal values for the respective pulmonary image based on the determined one or several lung vessel values. In particular, the signal value determination unit is configured to subdivide the segmented lung vessels into cross-sectional subelements and to determine the one or several lung vessel values based on a number of cross-sectional subelements. For subdividing the respective segmented lung vessel into cross-sectional subelements a predefined thickness of the respective cross-sectional subelement of the respective segmented lung vessel is preferentially assumed. The number of cross-sectional subelements in the respective pulmonary image provides a reliable measure for the detectability of the lung vessels in the pulmonary images, which can lead to improved signal values and hence to an improved determination of the image quality.

The signal value determination unit can be adapted to determine a single signal value for a respective pulmonary image or to determine several signal values for a respective pulmonary image, wherein in the latter case the different signal values for a same pulmonary image preferentially correspond to different sizes of the lung vessel. Thus, the sizes of the lung vessels might be subdivided into size classes and for each size class and for each pulmonary image a corresponding signal value can be determined. For instance, the sizes of the cross-sectional subelements can be determined and subdivided into size classes and the number of cross-sectional subelements with a size in a respective size class for a respective pulmonary image can be regarded as being the signal value for the respective size class, i.e. for the respective structure size, and for the respective pulmonary image. The size of a cross-sectional subelement can be determined as area-equivalent diameter. However, also another size measure might be used.

The noise value determination unit is preferentially configured to determine the one or several noise values for the respective pulmonary image based on image values of the respective pulmonary image, which represent the segmented lung vessels. Thus, preferentially the one or several noise values do not relate to the entire respective pulmonary image, but only to the part of the respective pulmonary image which shows the lung vessels. By using these noise values for determining the image quality, the determination of the image quality can be further improved. In particular, the noise value determination unit is configured to determine for each cross-sectional subelement a respective noise subvalue being indicative of the noise in the respective cross-sectional subelement and to determine the one or more noise values based on the determined noise subvalues.

The noise value determination unit can be adapted to determine a single noise value for a respective pulmonary image or to determine several noise values for a respective pulmonary image, wherein in the latter case the different noise values for a same pulmonary image preferentially correspond to different sizes of the lung vessel. Thus, the sizes of the lung vessels might be subdivided into size classes and for each size class and for each pulmonary image a corresponding noise value can be determined. For instance, the sizes of the cross-sectional subelements can be determined and subdivided into size classes and the average of noise subvalues of cross-sectional subelements with a size in a respective size class for a respective pulmonary image can be regarded as being the noise value for the respective size class, i.e. for the respective structure size, and for the respective pulmonary image. For determining a single noise value for a pulmonary image all noise subvalues, which have been determined for this pulmonary image, can be averaged.

Preferentially the determination of the signal values is based on the numbers of cross-sectional subelements and the determination of the noise values is based on the noise subvalues, which have been determined for these cross-sectional subelements, wherein this consideration of the cross-sectional subelements leads to a reliable determination of the signal values and the noise values and hence to a further improved determination of the image quality, which is based on these signal values and noise values.

In a preferred embodiment the signal value determination unit is adapted to determine the signal values for different sizes of the lung vessels in the different pulmonary images, wherein the noise value determination unit is adapted to determine the noise values for the different sizes of the lung vessels in the different pulmonary images, wherein the image quality determination unit is configured to provide reference signal values and reference noise values for different sizes of lung vessels and to determine the image quality such that it is indicative of a deviation of a) the determined signal values and the determined noise values from b) the provided reference signal values and reference noise values. Thus, a deviation of the determined signal and noise values from the provided reference signal and noise values is determined, wherein the image quality is indicative of this deviation.

In the provided, unsmoothed pulmonary image the lung nodule, if present, should be reliably detectable, wherein the detectability of the lung nodule in the pulmonary image often depends on the radiation dose applied to a patient for generating the pulmonary image, i.e. the higher the radiation dose applied to the image the larger is the detectability of the lung nodule in the pulmonary image. On the other hand, the radiation dose applied to the patient should not be higher than really required for reliably detecting the lung nodule, because the radiation dose itself can have an adverse effect to the patient, i.e. the radiation dose should be as low as reasonably achievable, wherein this requirement is also called "ALARA" principle. The reference signal and noise values are preferentially provided such that a pulmonary image having these values is in accordance with the ALARA principle. The determined image quality can then be a measure for the degree of conformity with the ALARA principle.

Preferentially, the image quality determination unit is configured to i) determine a first manifold based on the signal values and the noise values determined for the different sizes of the lung vessels, wherein the surface is determined in a space defined by a signal values dimension, a noise values dimension and a lung vessel size dimension, ii) determine a second manifold in the space based on the reference signal values and reference noise values provided for the different sizes of the lung vessels, iii) determine distances between the first and second manifolds for several locations on the first manifold, and iv) determine the image quality based on the distances. Moreover, the image quality determination unit is preferentially configured to determine an area of the first manifold, i.e. of a first surface, for which the determined distances are larger than a predefined distance threshold, and to determine the image quality based on this area. The area can be a single area or it can comprise several separate subareas. In particular, the image quality determination unit is configured to determine the image quality depending on the size of the area above the second manifold, i.e. above a second surface, and/or depending on the size of the area below the second manifold in the defined space. For instance, the image quality determination unit can be configured to determine an insufficient image quality, if the deviation measure indicates that the size of the area below the second manifold is larger than a predefined size threshold. Thus, as a deviation measure between the determined signal values and noise values and the reference signal values and noise values the size of the area above the second manifold defined by the reference values and/or the size of the area below this second manifold can be used for determining the image quality. By using the size of this area, which can comprise several separate subareas, the determination of the image quality can be further improved.

In an embodiment the pulmonary image providing unit is configured to provide a slice image having a slice thickness as the pulmonary image, wherein the signal value determination unit is adapted to normalize the respective signal value with respect to the slice thickness. The slice image can have one or several voxels in a slice direction, i.e. in a direction being perpendicular to the plane in which in this embodiment the pulmonary image mainly extends. Moreover, the signal value determination unit can be configured to determine a lung space as the space occupied by the lung within at least one of the pulmonary images and to normalize the respective signal value with respect to the determined lung space. Preferentially, the lung space, which might be a lung volume, is determined in the provided, unsmoothed pulmonary image. The lung space, i.e. the size of the space within the pulmonary image covered by the lung, can be determined by using known lung segmentation techniques. By using these normalizations the quality of the signal values and hence of the determination of the image quality, which is based, inter alia, on the signal values, can be further improved.

The system can further comprise a dose level determination unit configured to determine a radiation dose level to be applied for generating a next pulmonary image based on the determined image quality. In particular, the pulmonary image providing unit can be configured to provide the pulmonary image such that it is an image which has been generated by applying a certain radiation dose level to the lung, wherein the dose level determination unit can be configured to determine the radiation dose level to be applied for generating a next pulmonary image such that it is smaller than the certain radiation dose level, if the determined image quality is larger than a predefined quality threshold. For instance, if the image quality has been determined based on the size of the area of the first manifold above the second manifold as described above, wherein the predefined quality threshold corresponds to a predefined size threshold of the area, the image quality being larger than the predefined quality threshold can indicate that the image quality is higher than required for reliably detecting the lung nodule in the provided, unsmoothed pulmonary image, wherein this allows for a reduction of the radiation dose level applied to the lung. Also if the image quality is not determined by using the size of this area, but by using another measure for determining a deviation between the determined signal and noise values and the provided reference signal and noise values, a determined image quality being larger than the predefined quality threshold can indicate an unnecessarily high image quality, which allows for a reduction of the radiation dose level. This can lead to an improved alignment of a generation of a next pulmonary image with the ALARA principle.

The system can further comprise a user interface allowing a user to modify the provided pulmonary image, wherein the system can be adapted to determine the image quality based on the modified pulmonary image. Thus, all processing steps can be carried out based on the modified pulmonary image. This allows a user to interactively modify the pulmonary image and thereby determine how the properties of the provided unsmoothed pulmonary image influence the image quality. For instance, the user can interactively change settings such as dynamic window/level and the spatial screen resolution.

In a further aspect of the present invention a method for assessing a pulmonary image is presented, wherein the method comprises:

providing a pulmonary image, which comprises image elements to which image values are assigned and which shows lung vessels, by a pulmonary image providing unit, smoothing the provided pulmonary image to provide different pulmonary images with different degrees of smoothing by a smoothing unit, determining signal values for the different pulmonary images by a signal value determination unit, wherein for a respective pulmonary image one or more signal values, which are indicative of the detectability of the lung vessels in the respective pulmonary image, are determined based on the image values of the respective pulmonary image, determining noise values for the different pulmonary images by a noise value determination unit, wherein for a respective pulmonary image one or more noise values, which are indicative of the noise in the respective pulmonary image, are determined based on the image values of the respective pulmonary image, determining an image quality for the provided unsmoothed image based on the signal values and noise values determined for the different pulmonary images by an image quality determination unit.

In another aspect of the present invention a computer program for assessing a pulmonary image is presented, wherein the computer program comprises program code means for causing a system for assessing a pulmonary image as defined in claim 1 to carry out the steps of the method for assessing a pulmonary image as defined in claim 14, when the computer program is run on a computer controlling the system.

It shall be understood that a preferred embodiment of the present invention can also be any combination of the dependent claims or above embodiments with the respective independent claim.

These and other aspects of the invention will be apparent from and elucidated with reference to the embodiments described hereinafter.

DETAILED DESCRIPTION OF EMBODIMENTS

Figure 1:
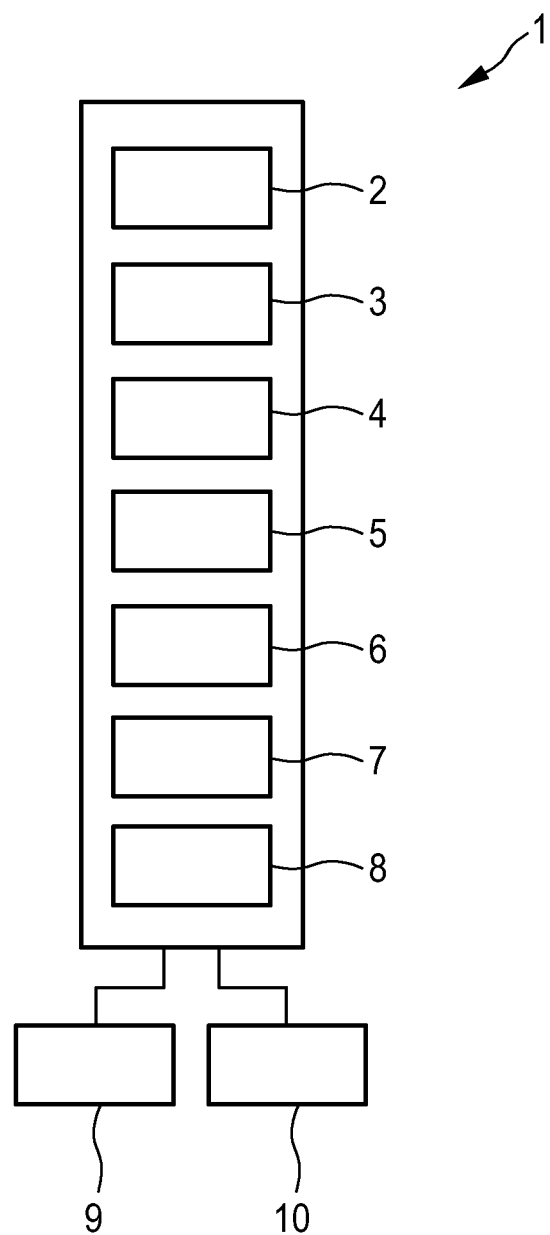
FIG. 1 shows schematically and exemplarily an embodiment of a system for assessing a pulmonary image.

FIG. 1 shows schematically and exemplarily an embodiment of a system for assessing a pulmonary image. The system 1 comprises a pulmonary image providing unit 2 configured to provide a pulmonary image which comprises image elements to which image values are assigned and which shows lung vessels. In this embodiment the pulmonary image providing unit 2 is a storing unit in which the pulmonary image is stored, wherein the storing unit is adapted to provide the stored pulmonary image. Moreover, in this embodiment the pulmonary image is a computed tomography image of a lung of a patient. The patient is preferentially a human being. However, the patient can also be an animal.

The system 1 further comprises a smoothing unit 3 for spatially smoothing the provided pulmonary image with different degrees of smoothing, in order to generate different, smoothed pulmonary images. In this embodiment the smoothing unit 3 is adapted to apply a Gaussian image smoothing. The resulting pulmonary images correspond to different levels of scale or, in other words, to different scale space levels.

The system 1 further comprises a signal value determination unit 4 configured to determine signal values for the differently smoothed pulmonary images and also for the provided, unsmoothed pulmonary image, wherein for a respective pulmonary image one or several signal values, which are indicative of the detectability of the lung vessels in the respective pulmonary image, are determined based on the image values of the respective pulmonary image. In this embodiment the signal value determination unit 4 is configured to segment the lung vessels in a respective pulmonary image based on the image values of the respective pulmonary image, to determine lung vessel values being indicative of the amount of lung vessels in the respective pulmonary image based on the segmented lung vessels and to determine several signal values for the respective pulmonary image based on the determined lung vessel values. In particular, the signal value determination unit 4 is configured to subdivide the segmented lung vessels into cross-sectional subelements, to determine the sizes of the cross-sectional subelements, to subdivide the sizes into size classes and to determine for each size class a respective lung vessel value based on the number of cross-sectional subelements having a size in the respective size class. For determining the cross-sectional subelements a predefined thickness of a respective cross-sectional subelement can be used. However, also another technique can be used for determining the cross-sectional subelements.

Figure 2:
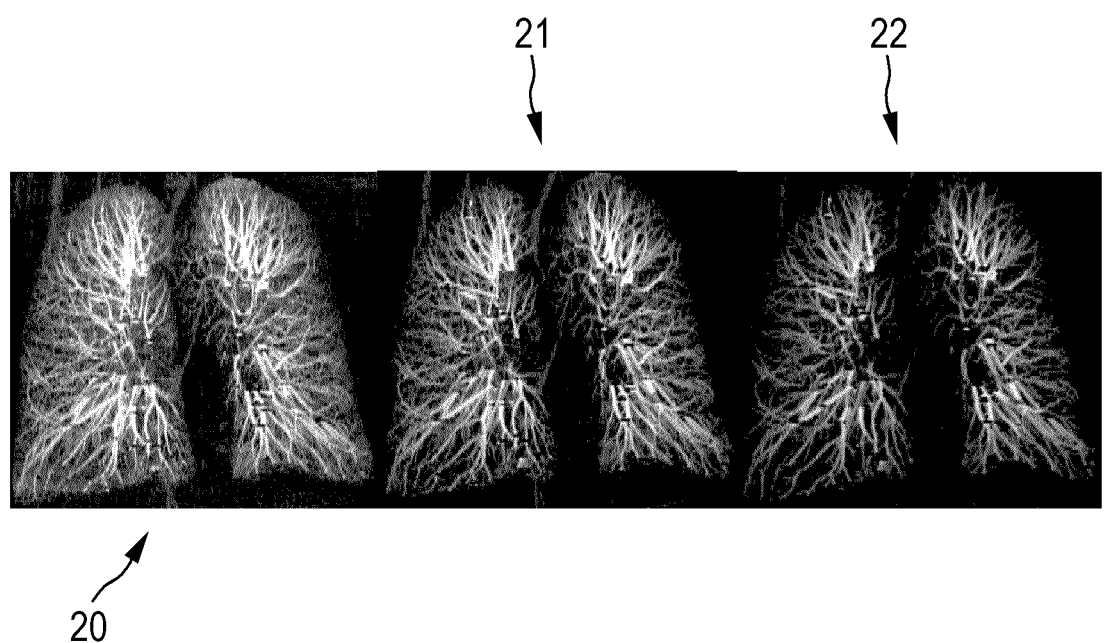
FIG. 2 illustrates a dependence of a number of detectable lung vessels on image smoothness.

FIG. 2 schematically and exemplarily shows three pulmonary images 20, 21, 22, which have been smoothed with different degrees of smoothing, wherein the degree of smoothing, i.e. the image smoothness, increases from left to right in FIG. 2. As can be seen, the number of detectable lung vessels decreases from left to right, i.e. with increasing image smoothness.

In this embodiment the pulmonary image providing unit 2 is configured to provide as the unsmoothed pulmonary image a slice image having a slice thickness, wherein the signal value determination unit 4 is adapted to normalize the respective signal value with respect to the slice thickness. Moreover, the signal value determination unit 4 is configured to determine the lung volume within the provided, unsmoothed pulmonary image and to normalize the respective signal value with respect to the determined lung volume. Thus, the size of the volume occupied by the lung within the provided, unsmoothed pulmonary image can be determined by, for instance, segmenting the lung within this pulmonary image, wherein the resulting size can be used for normalizing the determined signal values.

The system 1 further comprises a noise value determination unit 5 configured to determine noise values for the differently smoothed pulmonary image and in the provided, unsmoothed pulmonary image, wherein for a respective pulmonary image one or several noise values, which are indicative of the noise in the respective pulmonary image, are determined based on the image values of the respective pulmonary image. In particular, the noise value determination unit 5 is configured to determine the one or several noise values such that they are indicative of the noise in the image values representing the lung vessels in the respective pulmonary image. Thus, the noise value determination unit 5 is adapted to determine the one or several noise values for the respective pulmonary image based on image values of the respective pulmonary image, which represent the segmented lung vessels. In this embodiment the noise value determination unit 5 is configured to determine for each cross-sectional subelement a respective noise subvalue being indicative of the noise in the respective cross-sectional subelement and to determine a noise value for a respective size, i.e. for a respective size class, based on the noise subvalues determined for the cross-sectional subelements in the respective size class. For determining the noise values the absolute magnitude of Hounsfield Laplacians can be used by the noise value determination unit 5. However, also other known techniques for determining noise values based on image values of an image can be used for determining the noise values by the noise value determination unit 5.

The system further comprises an image quality determination unit 6 configured to determine an image quality for the provided unsmoothed image based on the signal values and noise values determined for the differently smoothed pulmonary images and for the provided, unsmoothed pulmonary image. In particular, the image quality determination unit 6 is configured to provide reference signal values and reference noise values for different sizes of the lung vessels and to determine the image quality such that it is indicative of a deviation of a) the signal values and the noise values determined for the different sizes from b) the reference signal values and reference noise values provided for the different sizes. In this embodiment the image quality determination unit 6 is configured to i) determine a first surface based on the signal values and noise values determined for the different sizes, wherein the surface is determined in a three-dimensional space defined by possible values of the signal values, of the noise values and of the different sizes of the lung vessels, ii) determine a second surface in the three-dimensional space based on the reference signal values and reference noise values provided for the different sizes, iii) determine distances between the first and second surfaces for several locations on the first surfaces, and iv) determine the image quality based on the distances. For instance, the image quality determination unit 6 can be configured to determine an area of the first surface, for which the determined distances are larger than a predefined distance threshold and to determine the image quality based on this area which can be a single area or which can comprise several separate subareas, wherein all subareas can be above the second surface, below the second surface or wherein some subareas can be above the second surface and some areas can be below the second surface. In particular, the image quality determination unit 6 can be configured to determine the image quality depending on the size of the area above the second surface and/or depending on the size of the area below the second surface in the three-dimensional image. In an embodiment the image quality determination unit 6 is configured to determine that the image quality is too high and can be reduced, if the size of the area above the second surface is larger than a predefined first size threshold. Moreover, the image quality determination unit 6 can be configured to determine that the image quality is too low and hence insufficient for reliably detecting lung nodules, if the size of the area below the second surface, for which the determined distances are larger than the predefined distance threshold, is larger than a predefined second size threshold. The first and second size thresholds can be the same or they can be different. All thresholds like the size thresholds and the distance thresholds can be predetermined by calibration procedures and/or they can be modifiable by a user. The image quality determination unit 6 can be further adapted to determine that the image quality is as desired, especially in accordance with the ALARA principle, if the size of the area of the first surface, for which the determined distances are larger than a predefined distance threshold, above the first surface is smaller than the first size threshold and below the second surface smaller than the second size threshold.

The system 1 further comprises a dose level determination unit 7 configured to determine a radiation dose level to be applied for generating a next pulmonary image based on the determined image quality. In this embodiment the pulmonary image providing unit 2 is configured to provide the pulmonary image such that it is an image which has been generated by applying a certain radiation dose level to the lung, wherein the dose level determination unit 7 is configured to determine the radiation dose level to be applied for generating a next pulmonary image such that it is smaller than the certain radiation dose level, if the determined image quality is larger than a predefined quality threshold. This means particularly that the radiation dose level to be applied for generating a next pulmonary image is determined such that it is smaller than the certain radiation dose level, if the size of the area of the first surface, for which the determined distances are larger than the predefined distance threshold, above the second surface is larger than the first size threshold.

The system 1 further comprises a user interface 8 allowing a user to modify the provided, unsmoothed pulmonary image, wherein the system 1 is adapted to determine the image quality based on the modified pulmonary image. Thus, all processing steps can be carried out based on the modified pulmonary image. The user can therefore change settings such as dynamic window/level and/or a spatial screen resolution, wherein then the procedures like the smoothing, signal value determination, noise value determination and image quality determination procedures are carried out based on the modified pulmonary image.

The system 1 further comprises an input unit 9 like a keyboard, a computer mouse, a touch screen, et cetera and an output unit 10 including a display for showing, for instance, the pulmonary images and for indicating the determined image quality. The output unit 10 can also comprise an acoustic unit for acoustically indicating the determined image quality.

Figure 3:
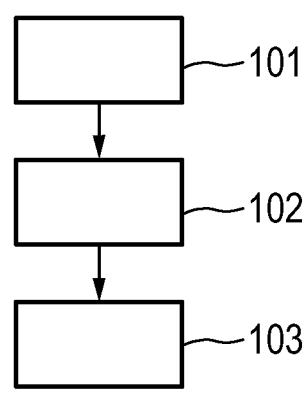
FIG. 3 shows a flowchart exemplarily illustrating an embodiment of a method for assessing a pulmonary image.

In the following an embodiment of a method for assessing a pulmonary image will be described with reference to a flowchart shown in FIG. 3.

In step 101 a pulmonary image, which comprises image elements to which image values are assigned and which shows lung vessels, is provided by the pulmonary image providing unit 2. In step 102 the provided pulmonary image is smoothed to different degrees of smoothing by the smoothing unit 3, signal values are determined for the differently smoothed pulmonary images and for the unsmoothed pulmonary image by the signal value determination unit 4, wherein for a respective pulmonary image signal values, which are indicative of the detectability of the lung vessels having a respective size in the respective pulmonary image, are determined based on the image values of the respective pulmonary image, and noise values are determined for the different pulmonary images by the noise value determination unit 5, wherein for a respective pulmonary image noise values, which are indicative of the noise in the respective pulmonary image, are determined for different sizes of the lung vessels based on the image values of the respective pulmonary image. In step 103 an image quality of the provided unsmoothed image is determined based on the signal values and the noise values determined for the different pulmonary images by the image quality determination unit 6.

Generally, screening for lung cancer with low dose computed tomography scanning is recognized as efficient for detecting lung nodules, wherein assurance of image quality is highly required, especially for avoiding oversights. The screening of the lung cancer should use a radiation dose as low as reasonably achievable on the one hand, while on the other hand an image quality level should be maintained, which is sufficient to ensure detection of possible lung tumors, i.e. of possible lung nodules. Thus, the screening for lung cancer should be in accordance with the ALARA principle. The system and method described above for assessing a pulmonary image allows for a determination of whether the image quality, i.e. the image quality level, of the provided pulmonary image is sufficient to achieve the ALARA principle. Moreover, the system and method for assessing a pulmonary image is vendor-agnostic, and it can be retrospectively applied on a batch of readily reconstructed pulmonary images which might be received from a Picture Archiving and Communication System (PACS). Furthermore, the determined image quality is specific for the respective pulmonary image and hence for the respective patient and a respective imaging protocol which has been used for generating the provided pulmonary image. The lung vessels detectable in the provided pulmonary image are of course patient specific and they are very likely and very reliably present in a pulmonary image such that the lung vessels with the different sizes are very well suited as markers for image quality.

The system and method for assessing a pulmonary image provides an automatic quantitative assessment of a pulmonary image based on signal values, i.e. the detectability, of lung vessels of different sizes in the provided pulmonary image and based on noise values determined for the parts of the pulmonary images represented by the lung vessels, wherein also the noise values are determined for different sizes of the lung vessels. The lung vessels are always present in pulmonary images, wherein the large range of lung vessel sizes and, in the case of computed tomography, Hounsfield densities cover the respective ranges of potential lung nodules well. The notion is that, if a clear deficiency in the number of detectable, especially visible, lung vessels is observed, then this can be a strong indicator for insufficient image quality for reliably detecting potential nodules. The vessel density may vary between patients, but averages out over a group of patients much more evenly than the number of tumors, i.e. than the number of lung nodules. Thus, determining an average image quality by averaging the image qualities determined for different images of different patients can lead to a more robust quality measure, i.e. a more robust image quality, which can be indicative of the quality of the imaging system or, more generally, of, for instance, a screening center at which the images have been generated.

The above described first surface is a first manifold in the space spanned by three dimensions signal, noise and structure size, i.e. the sizes of the lung vessels in the pulmonary images, wherein this first manifold is used for assessing the quality of the provided pulmonary image. If a too large part of this first manifold is lower than an ideal reference manifold, i.e. than the second surface, it is assumed that the provided pulmonary image does not meet necessary image quality requirements. In another embodiment the second surface, i.e. the reference manifold, might correspond to manifolds from another imaging system, i.e. an imaging system which has not been used for generating the provided pulmonary image, like an imaging system of another screening center, if the provided pulmonary image has been generated by an imaging system of a screening center, in order to compare image qualities of, for instance, different screening centers. The system and method for assessing a pulmonary image does not consider only a single signal/noise operating point, but establishes and compares the determined first manifold, i.e. the determined first surface, for the range of possible sizes of possible lung nodules in the pulmonary image.

The pulmonary image providing unit 2 can be adapted to provide the pulmonary image by identifying a lung volume in a provided overall thoracic computed tomography volume image and by segmenting the identified lung volume out of the overall thoracic computed tomography volume image, in order to provide a pulmonary image which substantially only includes the lung volume and not parts outside of the lung volume. The segmentation of the lung vessels in the respective pulmonary image can be regarded as being an automatic detection of image structures in the respective pulmonary image conformant with the lung vessels, wherein this segmentation procedure can use known segmentation techniques like a connected component analysis for a multitude of Hounsfield thresholds and wherein from the resulting structures, structures having a two-dimensional cross section with an area size being lower than a predefined upper area size limit can be selected. Corresponding resulting segmented lung vessels are schematically and exemplarily shown in FIG. 2.

The system and method for assessing a pulmonary image compute for each vessel-like structure object, i.e. in the above described embodiments for each cross-sectional subelement of the segmented lung vessels, the size and the noise by using, for instance, the area-equivalent diameter as the size and the absolute magnitude of Hounsfield Laplacians for determining the noise. In a preferred embodiment the number of detected vessel cross-sectional subelements per lung volume, which can also be regarded as being a frequency, is accumulated into a histogram for the different pulmonary images depending on the structure sizes and the noise values. A resulting graph, which also considers a normalization with respect to the thickness of the slices of the pulmonary images and a normalization over the volume of the lung in the pulmonary images, is exemplarily shown in FIG. 4 for a single structure size.

Figure 4:
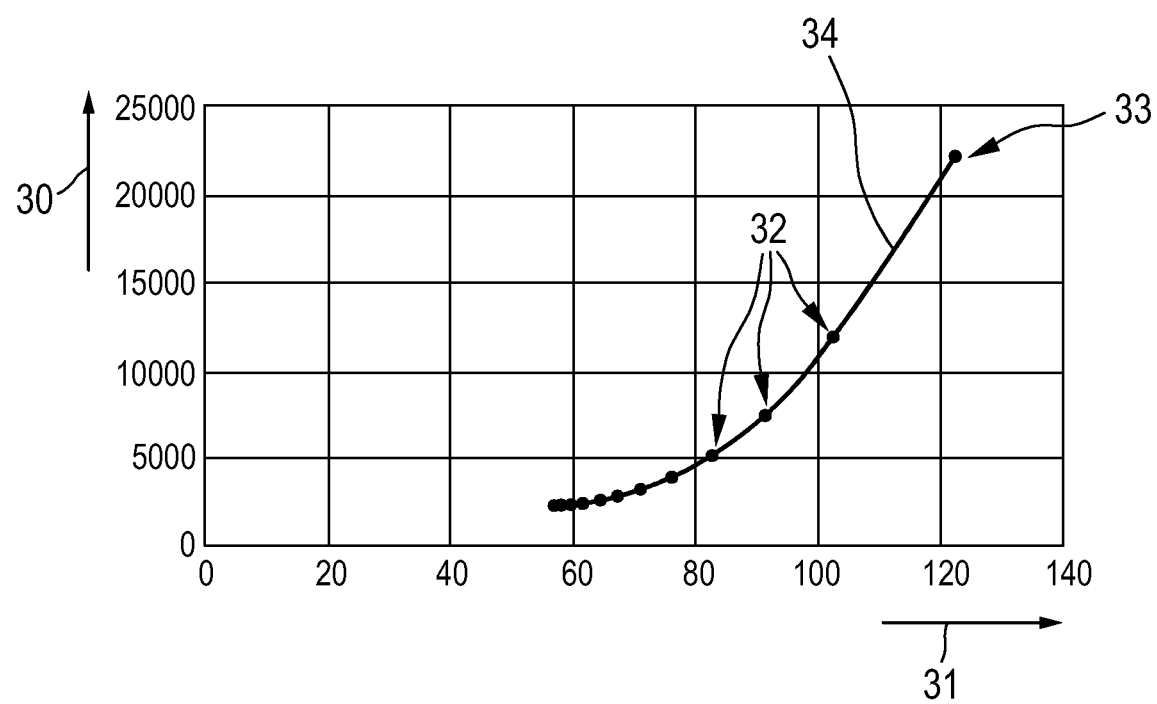
FIG. 4 shows exemplarily a curve illustrating a change of a number of cross-sectional subelements of lung vessels and of noise with different degrees of smoothing for a single structure size.

In FIG. 4 the arrow 30 indicates the direction of an increasing number of cross-sectional subelements, i.e. increasing signal values, and the arrow 31 indicates an increasing noise, i.e. increasing noise values. Moreover, in FIG. 4 the points 32 correspond to differently smoothed pulmonary images and the point 33 corresponds to the initially provided, unsmoothed pulmonary image. The line 34 is a point through these points. Thus, FIG. 4 shows the number of vessel cross sections, which might also be regarded as being a frequency of vessel cross sections because of being normalized with respect to the lung volume, and the noise values for different degrees of smoothing and a single structure size, wherein in this example, as described above, the noise is estimated as absolute magnitude of Hounsfield Laplacians, i.e. as a deviation from a linear interpolation of neighbor voxels. The original pulmonary image prior to any smoothing has the highest noise and the highest number of vessel cross sections as indicated by the point 33. With increasing degree of smoothing, which may be obtained by successively applying a smoothing operation like a Gaussian smoothing operation to the pulmonary image, the noise level in the cross sections is reduced, but also the number of detectable cross sections diminishes.

Figure 5:
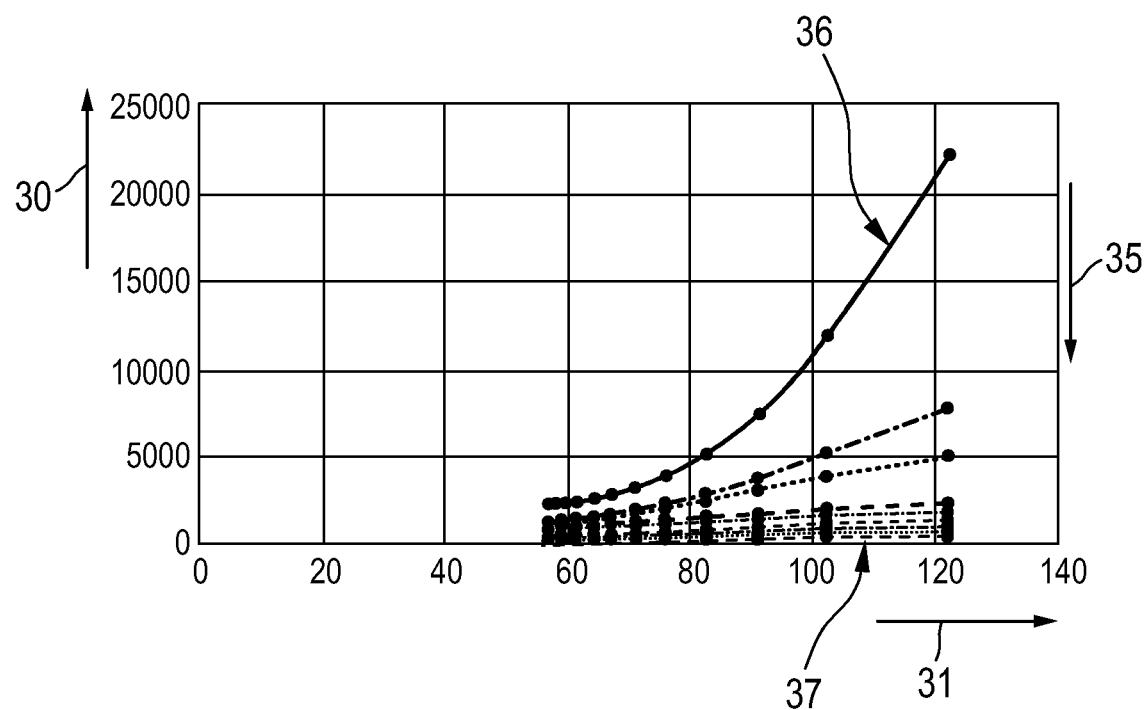
FIG. 5 shows exemplarily a graph illustrating an influence of structure sizes on the curve shown in FIG. 4, and FIGS. 6 and 7 show exemplarily graphs illustrating how the number of detectable cross-sectional subelements of lung vessels and the noise differ for different provided pulmonary images.

FIG. 4 shows the relation between the number of vessel cross sections, i.e. between the signal value, and the noise value for a specific structure size or for a specific size class, i.e. in this embodiment for one area-equivalent diameter or diameter class of the cross-sectional subelements detectable in the pulmonary images. FIG. 5 shows exemplarily the relation between the number of cross sections and noise for different structure sizes, i.e. in this example for different area-equivalent diameters of the segmented lung vessels. In FIG. 5 the arrow 35 indicates the direction of increasing structure sizes such that the curve 36 corresponds to the smallest structure size and the curve 37 corresponds to the largest structure size. As can be seen in FIG. 5, the number of detectable lung vessels and hence the number of detectable cross-sectional subelements of the lung vessels decreases predominantly for the small structure sizes, while staying relatively stable for larger structure sizes. These curves together span a first surface, i.e. a first manifold, in a three-dimensional space defined by the number of vessel cross sections, i.e. the possible signal values, as indicated by the arrow 30, by the possible noise values as indicated by the arrow 31 and by the possible structure sizes as indicated by the arrow 35. Thus, the three-dimensional space is spanned by a signal dimension 30, a noise dimension 31 and a structure size dimension 35. Preferentially, the first surface is determined based on the curves shown in FIG. 5 such that the first surface is a directed surface having a direction pointing towards higher detection frequencies. This first surface is preferentially determined by fitting to the signal value—noise value—structure size points in the three-dimensional space, wherein in this embodiment the signal value is defined by the number of cross-sectional subelements of the segmented lung vessels having the respective structure size. The fitting can be, for instance, a piecewise linear fitting, a polynomial fitting, a spline fitting, a support vector fitting, et cetera.

Figure 6:
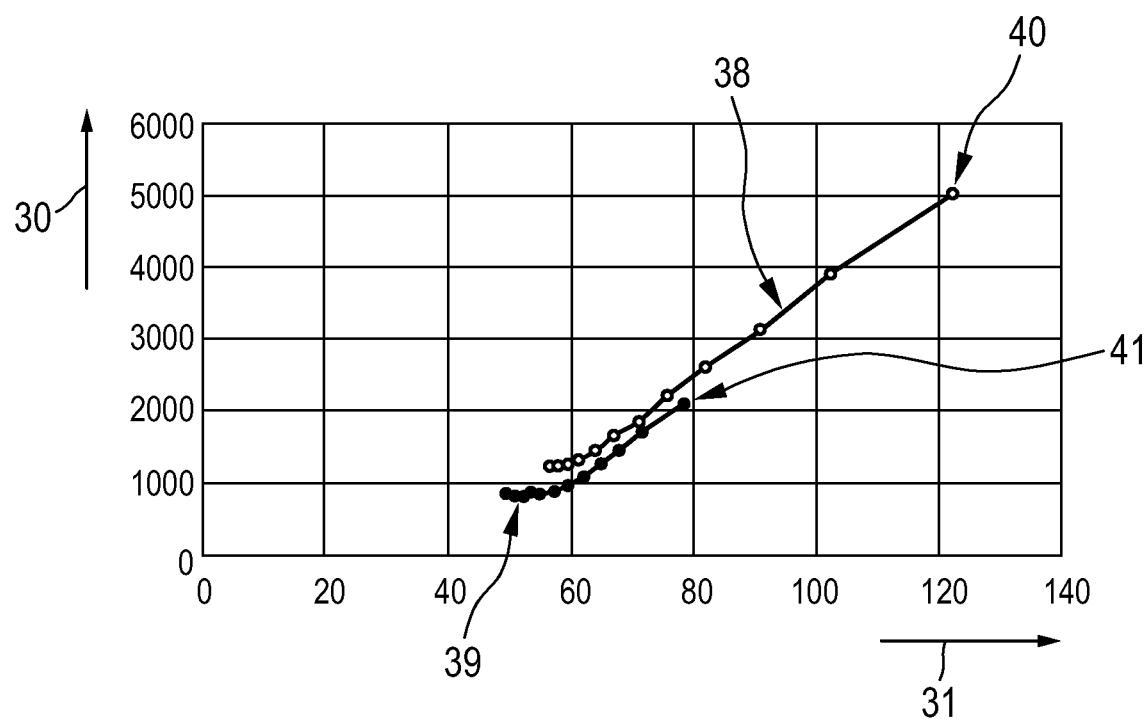

FIG. 6 exemplarily shows two curves 38, 39, which correspond to different reconstructions of a same computed tomography scan, i.e. the same computed tomography projection data have been used for differently reconstructing two different pulmonary images, wherein a first curve 38 has been determined based on a first reconstructed computed tomography image and a second curve 39 has been determined based on a second reconstructed computed tomography image. In this example, the first reconstructed computed tomography image has been reconstructed such that it corresponds to a relatively high spatial frequency and the second reconstructed image has been reconstructed such that it corresponds to a relatively low spatial frequency. In this sense the first image could also be regarded as being a hard image and the second image could also be regarded as being a soft image. The respective provided, unsmoothed image is indicated by the points 40, 41, respectively. The first, high-frequency image has more noise and more structures, i.e. more cross-sectional subelements of the segmented lung vessels than the second, low-frequency image. However, with increasing degree of smoothing, i.e., for instance, after successive Gaussian smoothings, it becomes apparent that the curves are quite close, indicating similar image quality. FIG. 6 shows the curves for a single structure size, i.e. in this embodiment for a single area-equivalent diameter. Corresponding curves will be determined also for other structure sizes such that the curves span a respective surface in the above defined three-dimensional space, wherein with increasing degree of smoothing these two surfaces are quite close.

Figure 7:
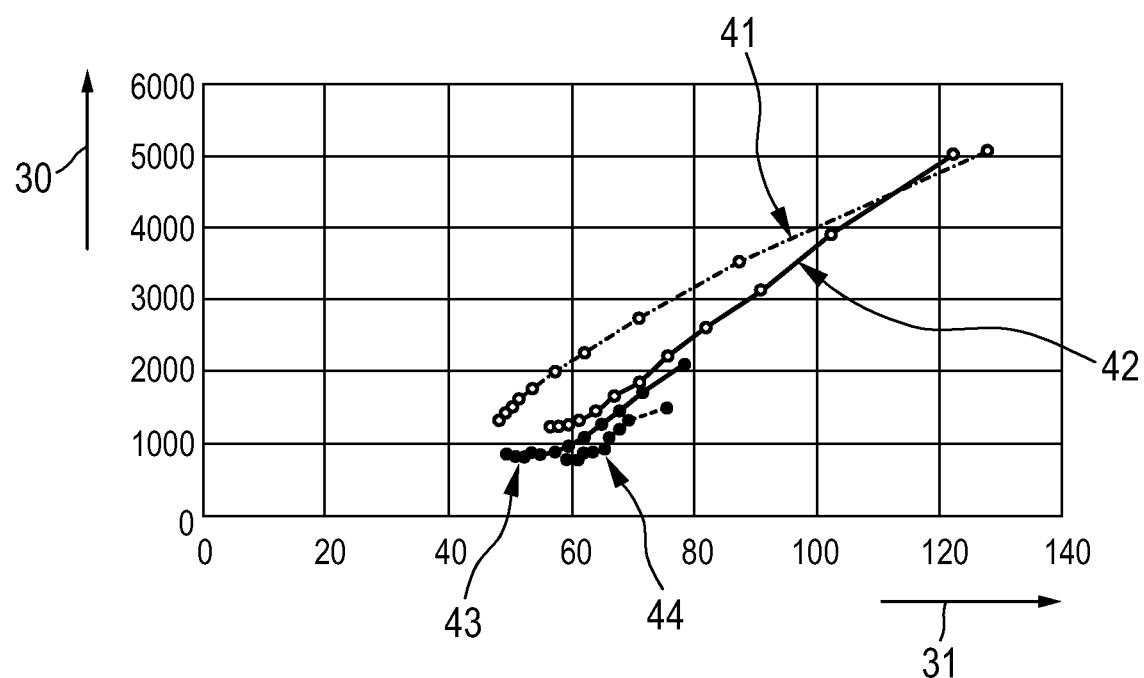

FIG. 7 shows schematically and exemplarily four curves 41 . . . 44 for a single structure size, i.e. for a single size class, wherein the different curves 41 . . . 44 correspond to four different provided pulmonary images. As can be seen, the curve 41 corresponds to a provided pulmonary image showing significantly more structures at almost all noise levels than the other provided pulmonary images. Also here, for various structure sizes (in FIG. 7 the curves correspond to a single structure size only) the four curves 41 . . . 44 generalize to four two-dimensional surfaces which can be compared, for instance, by height or relative distances.

In an embodiment the two-dimensional surface, i.e. the first surface, in the three-dimensional space is determined for a provided pulmonary image and this two-dimensional first surface is compared with a reference surface, which corresponds to a desired image quality, in order to yield a metric for the image quality of the provided pulmonary image. For instance, a signed distance of the first surface to the second, reference surface can be determined and used for assessing the image quality of the provided pulmonary image. Reference surfaces, which can also be regarded as being image quality surfaces, can be taken from a reference base or a certain screening center. The references can optionally be stratified by patient cohorts like male/female, age, body mass index, et cetera. Thus, for each patient a reference surface can be provided which corresponds to the respective patient with respect to features like gender, age, et cetera. In an embodiment the image quality determination unit 6 is adapted to determine that the image quality of the provided pulmonary image is insufficient for lung nodule detection, if too many areas of the directed surface are below the reference quality surface, i.e. below the second surface. Vice versa, if too many areas of the surface are above the second surface, it can be determined that the image acquisition dose could and should be lowered to satisfy the ALARA principle. The determination whether too many areas are below or above the second surface can be based on predefined area size thresholds as described above, which might be determined, for instance, by calibration. By using the user interface this quality check can be implemented for interactive viewing software. The user can change settings such as dynamic window/level, spatial screen resolution, et cetera, wherein the quality check, i.e. the determination of the image quality, can be performed for each interactively chosen setting, wherein the user can be warned, if the resulting display quality appears to be insufficient for exhaustive detection of nodules.

The above described system and method for assessing a pulmonary image do not require scanning of a physical phantom. The provided quantitative image quality measure is preferentially not for a general scan type or reconstruction type, but it is specific to the respective patient, i.e., for instance, to the patient's size, body mass, bones, et cetera. Moreover, it is specific to the actual imaging protocol, i.e., for instance, in case of computed tomography imaging specific to the tube current, the tube voltage, et cetera. It is also specific to resolution changes along an actual course of dynamic dose modulation across the scan, i.e. to an automatic variation of the dose for denser areas and base and apex of the lung, if present. Furthermore, it is specific to a possible resolution loss due to suboptimal placement of the patient with respect to a field-of-view centering, i.e. it is specific to a possible tapering off of the resolution towards off-centered locations. It can also be specific to a suboptimal choice of a reconstruction field-of-view, i.e. unnecessary large field-of-views limit the voxel spacing. Finally, it is specific to the respectively chosen reconstruction algorithm, i.e., for instance, to the kernel, whether it is an iterative reconstruction, et cetera. The system and method for assessing a pulmonary image cover a range of interest of sizes and image values, i.e. in the case of computed tomography of Hounsfield densities, with respect to lung nodule detection. Moreover, the assessment of the quality of the pulmonary image can be applied retrospectively and for all manufacturers of imaging systems. It can also be applied to batches of images like images for a certain time period or a certain patient cohort or to individual images. If a batch of images is considered, for each image a respective image quality can be determined, wherein these image qualities can be combined for determining an image quality for the batch of images. For instance, the image qualities can be averaged and/or a standard deviation of these image qualities can be determined for determining the image quality for the batch of images. For determining an image quality for a respective image distances between the respective first surface and the reference surface can be combined, in particular averaged. Thus, the deviation between a two-dimensional noise-resolution surface and a reference surface can be condensed into a single signed scalar number by, for instance, averaging the distances below and above the reference surface, thereby generating for each image a number, wherein the numbers determined for the different images, which might correspond to different patients, can be averaged and/or a standard deviation can be determined, in order to determine the image quality for the batch of images. The image quality can be determined relatively fast such that, if required, a re-scan of a patient can be performed relatively fast, especially before a patient leaves a hospital. The system and method for assessing a pulmonary image can be applied to, for instance, a low dose screening computed tomography image, but also to other computed tomography images, and also to other images showing lung vessels which might not be generated by using a computed tomography imaging system.

Although in above described embodiments a three-dimensional space is considered, which is defined by a signal dimension, a noise dimension and a structure size dimension, in another embodiment a further dimension can be considered like the structure contrast, wherein in this case respective three-dimensional manifolds, i.e. three-dimensional surfaces, are defined in the corresponding four-dimensional space and compared for determining the image quality. In particular, with increasing degree of smoothing low contrast structures start to vanish earlier than high contrast structures. In an embodiment the structure contrast is defined as a difference of a mean brightness, i.e., for instance, of a mean Hounsfield density, of the vessel cross section to that of their neighborhood, i.e. of their directly adjacent image background.

Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality.

A single unit or device may fulfill the functions of several items recited in the claims. The mere fact that certain measures are recited in mutually different dependent claims does not indicate that a combination of these measures cannot be used to advantage.

Procedures like the provision of the pulmonary image, the smoothing of the provided pulmonary image, the segmentation of the lung vessels in the pulmonary images, the determination of the cross-sectional subelements of the lung values, the determination of the sizes of the cross-sectional subelements, the determination of the number of cross-sectional subelements, the determination of the noise values for the cross-sectional subelements, the determination of the image quality et cetera performed by one or several units or devices can be performed by any other number of units or devices. For instance, these procedures can be carried out by a single device. These procedures and/or the control of the system for assessing a pulmonary image in accordance with the method for assessing a pulmonary image can be implemented as program code means of a computer program and/or as dedicated hardware.

A computer program may be stored/distributed on a suitable medium, such as an optical storage medium or a solid-state medium, supplied together with or as part of other hardware, but may also be distributed in other forms, such as via the Internet or other wired or wireless telecommunication systems.

Any reference signs in the claims should not be construed as limiting the scope.

The invention relates to a system for assessing a pulmonary image which allows for an improved assessment with respect to lung nodules detectability. The pulmonary image is smoothed for providing different pulmonary images with different degrees of smoothing, wherein signal values and noise values, which are indicative of the lung vessel detectability and the noise in these images, are determined and used for determining an image quality being indicative of the usability of the pulmonary image to be assessed for detecting lung nodules. Since a pulmonary image shows lung vessels with many different vessel sizes and with many different image values, which cover the respective ranges of potential lung nodules generally very well, the image quality determination based on the different pulmonary images with different degrees of smoothing allows for a reliable assessment of the pulmonary image's usability for detecting lung nodules.

The invention claimed is:

1. A system for assessing a pulmonary image, the system comprising:
   a memory that stores a plurality of instructions; and
   at least one processor that couples to the memory and is configured to execute the plurality of instructions to:
   provide the pulmonary image comprising image elements having assigned image values, the pulmonary image showing lung vessels;
   smooth the provided pulmonary image for providing different pulmonary images with different degrees of smoothing;
   determine signal values for the different pulmonary images, wherein for a respective pulmonary image one or several signal values, which are indicative of detectability of the lung vessels in the respective pulmonary image, are determined based on the image values of the respective pulmonary image;
   determine noise values for the different pulmonary images, wherein for the respective pulmonary image one or several noise values, which are indicative of the noise in the respective pulmonary image, are determined based on the image values of the respective pulmonary image;
   determine an image quality for an unsmoothed pulmonary image based on the signal values and noise values determined for the different pulmonary images; and
   determine a radiation dose level to be applied for generating a next pulmonary image based on the determined image quality.

2. The system according to claim 1, wherein the at least one processor is configured to segment the lung vessels in the respective pulmonary image based on the image values of the respective pulmonary image, determine one or several lung vessel values being indicative of the amount of lung vessels in the respective pulmonary image based on the segmented lung vessels, and determine the one or several signal values for the respective pulmonary image based on the determined one or several lung vessel values.

3. The system according to claim 2, wherein the at least one processor is configured to subdivide the segmented lung vessels into cross-sectional sub-elements and determine the one or several lung vessel values based on a number of cross-sectional sub-elements.

4. The system according to claim 2, wherein the at least one processor is configured to determine the one or several noise values for the respective pulmonary image based on image values of the respective pulmonary image, the image values representing the segmented lung vessels.

5. The system according to claim 3, wherein the at least one processor is configured to determine for each cross-sectional sub-element a respective noise sub-value being indicative of the noise in the respective cross-sectional sub-element and determine the one or several noise values based on the determined noise sub-values.

6. The system according to claim 1, wherein the at least one processor is configured to determine the signal values for different sizes of the lung vessels in the different pulmonary images, determine the noise values for the different sizes of the lung vessels in the different pulmonary images, provide reference signal values and reference noise values for the different sizes of lung vessels and determine the image quality such that it is indicative of a deviation of the determined signal values and the determined noise values from the provided reference signal values and reference noise values.

7. The system according to claim 6, wherein the at least one processor is configured to determine a first manifold based on the signal values and the noise values determined for the different sizes of the lung vessels, wherein the surface is determined in a space defined by a signal values dimension, a noise values dimension and a lung vessel size dimension, determine a second manifold in the space based on the reference signal values and reference noise values provided for the different sizes of the lung vessels, determine distances between the first and second manifolds for several locations on the first manifold, and determine the image quality based on the distances.

8. The system according to claim 7, wherein the at least one processor is configured to determine an area of the first manifold having the determined distances larger than a predefined distance threshold, and determine the image quality based on this area.

9. The system according to claim 8, wherein the at least one processor is configured to determine the image quality depending on the size of the area above the second manifold and/or depending on the size of the area below the second manifold in the three-dimensional space.

10. The system according to claim 1, wherein the at least one processor is configured to determine a lung space as the space occupied by the lung within at least one of the pulmonary images and normalize the respective signal value with respect to the determined lung space.

11. The system according to claim 1, wherein the at least one processor is configured to provide a slice image having a slice thickness as the pulmonary image, and normalize the respective signal value with respect to the slice thickness.

12. The system according to claim 1, wherein the at least one processor is configured to provide the pulmonary image generated by applying a certain radiation dose level to the lung, and determine the radiation dose level to be applied for generating a next pulmonary image being smaller than the certain radiation dose level, if the determined image quality is larger than a predefined quality threshold.

13. A method for assessing a pulmonary image, the method comprising:

providing the pulmonary image comprising image elements having assigned image values, the pulmonary image showing lung vessels;

smoothing the provided pulmonary image to provide different pulmonary images with different degrees of smoothing;

determining signal values for the different pulmonary images, wherein for a respective pulmonary image one or more signal values, which are indicative of the detectability of the lung vessels in the respective pulmonary image, are determined based on the image values of the respective pulmonary image;

determining noise values for the different pulmonary images, wherein for the respective pulmonary image one or more noise values, which are indicative of the noise in the respective pulmonary image, are determined based on the image values of the respective pulmonary image;

determining an image quality for an unsmoothed pulmonary image based on the signal values and noise values determined for the different pulmonary images; and determining a radiation dose level to be applied for generating a next pulmonary images based on the determined image quality.

14. A non-transitory computer readable medium for storing executable instructions that, when executed, cause a method to be performed for assessing a pulmonary image, the method comprising:

providing the pulmonary image comprising image elements having assigned image values, the pulmonary image showing lung vessels;

smoothing the provided pulmonary image to provide different pulmonary images with different degrees of smoothing;

determining signal values for the different pulmonary images, wherein for a respective pulmonary image one or more signal values, which are indicative of the detectability of the lung vessels in the respective pulmonary image, are determined based on the image values of the respective pulmonary image;

determining noise values for the different pulmonary images, wherein for the respective pulmonary image one or more noise values, which are indicative of the noise in the respective pulmonary image, are determined based on the image values of the respective pulmonary image;

determining an image quality for an unsmoothed pulmonary image based on the signal values and noise values determined for the different pulmonary images; and determining a radiation dose level to be applied for generating a next pulmonary images based on the determined image quality.

\* \* \* \* \*